(12) United States Patent
Lish et al.

(10) Patent No.: US 9,486,256 B1
(45) Date of Patent: Nov. 8, 2016

(54) ROD REDUCTION ASSEMBLIES AND RELATED METHODS

(71) Applicant: NuVasive, Inc., San Diego, CA (US)

(72) Inventors: Scott Lish, Oceanside, CA (US); Justin Doose, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 29 days.

(21) Appl. No.: 14/217,101

(22) Filed: Mar. 17, 2014

Related U.S. Application Data

(60) Provisional application No. 61/802,046, filed on Mar. 15, 2013.

(51) Int. Cl.
*A61B 17/70* (2006.01)

(52) U.S. Cl.
CPC .................................. *A61B 17/7085* (2013.01)

(58) Field of Classification Search
CPC .......................... A61B 17/70–17/7046; A61B 17/7074–17/7092
See application file for complete search history.

(56) References Cited

U.S. PATENT DOCUMENTS

| | | | |
|---|---|---|---|
| 929,067 A * | 7/1909 | Williamson | .................. 285/317 |
| 4,282,217 A | 8/1981 | Baglioni | |
| 4,450,899 A | 5/1984 | Jakobsson | |
| 4,927,425 A | 5/1990 | Lozier | |
| 4,955,885 A | 9/1990 | Meyers | |
| 5,020,519 A | 6/1991 | Hayes | |
| 5,217,497 A | 6/1993 | Mehdian | |
| D346,217 S | 4/1994 | Sparker | |
| 5,360,431 A | 11/1994 | Puno | |
| 5,496,321 A | 3/1996 | Puno | |
| 5,616,143 A | 4/1997 | Schlapfer | |
| 5,624,442 A | 4/1997 | Mellinger | |
| 5,681,319 A | 10/1997 | Biedermann | |
| 5,716,356 A | 2/1998 | Biedermann | |
| 5,720,751 A | 2/1998 | Jackson | |
| 5,782,831 A | 7/1998 | Sherman | |
| 5,782,833 A | 7/1998 | Haider | |
| 5,810,878 A | 9/1998 | Burel | |
| 5,910,141 A | 6/1999 | Morrison | |
| 5,941,885 A | 8/1999 | Jackson | |
| 5,944,720 A | 8/1999 | Lipton | |
| 6,004,349 A | 12/1999 | Jackson | |
| 6,059,786 A | 5/2000 | Jackson | |
| 6,123,707 A | 9/2000 | Wagner | |
| 6,139,549 A | 10/2000 | Keller | |
| 6,183,472 B1 | 2/2001 | Lutz | |
| 6,189,422 B1 | 2/2001 | Stihl | |
| 6,224,598 B1 | 5/2001 | Jackson | |
| 6,248,107 B1 | 6/2001 | Foley | |

(Continued)

FOREIGN PATENT DOCUMENTS

| | | |
|---|---|---|
| CN | 101103935 A | 1/2008 |
| CN | 201328875 Y | 10/2009 |

(Continued)

*Primary Examiner* — Jan Christopher Merene
*Assistant Examiner* — Steven Cotroneo
(74) *Attorney, Agent, or Firm* — Rory Schermerhorn

(57) ABSTRACT

This disclosure describes example embodiments of rod reduction instrumentation. The rod reducers can be used during the installation of a rod based surgical fixation system to help urge the rod into the fixation anchors. The reducers described provide various configurations delivering large reduction distance capabilities, strong controlled reduction coupled with an ability to quickly advance the reducer if desired, and reduction of bulk through the surgical corridor.

13 Claims, 11 Drawing Sheets

(56) References Cited

U.S. PATENT DOCUMENTS

| | | | |
|---|---|---|---|
| 6,251,111 B1 | 6/2001 | Barker | |
| 6,251,112 B1 | 6/2001 | Jackson | |
| 6,258,090 B1 | 7/2001 | Jackson | |
| 6,379,356 B1 | 4/2002 | Jackson | |
| 6,440,132 B1 | 8/2002 | Jackson | |
| 6,440,133 B1 | 8/2002 | Beale | |
| 6,520,963 B1 | 2/2003 | Mckinley | |
| 6,554,834 B1 | 4/2003 | Crozet | |
| 6,575,981 B1 | 6/2003 | Boyd | |
| 6,648,888 B1 * | 11/2003 | Shluzas | A61B 17/7091 606/86 A |
| 6,660,006 B2 | 12/2003 | Markworth | |
| 6,726,692 B2 | 4/2004 | Bette | |
| 6,740,089 B2 | 5/2004 | Haider | |
| 6,743,231 B1 | 6/2004 | Gray | |
| 6,884,244 B1 | 4/2005 | Jackson | |
| 6,981,973 B2 | 1/2006 | Mckinley | |
| 7,156,849 B2 | 1/2007 | Dunbar | |
| 7,278,995 B2 * | 10/2007 | Nichols | A61B 17/7032 606/272 |
| 7,371,239 B2 | 5/2008 | Dec | |
| 7,462,182 B2 | 12/2008 | Lim | |
| 7,470,279 B2 | 12/2008 | Jackson | |
| 7,481,813 B1 | 1/2009 | Purcell | |
| 7,491,207 B2 | 2/2009 | Keyer | |
| 7,520,879 B2 | 4/2009 | Justis | |
| 7,572,281 B2 | 8/2009 | Runco | |
| 7,591,836 B2 | 9/2009 | Dick | |
| 7,597,694 B2 | 10/2009 | Lim | |
| 7,608,081 B2 | 10/2009 | Abdelgany | |
| 7,611,517 B2 | 11/2009 | Lim | |
| 7,621,918 B2 | 11/2009 | Jackson | |
| 7,625,376 B2 | 12/2009 | Brumfield | |
| 7,651,502 B2 | 1/2010 | Jackson | |
| 7,678,139 B2 | 3/2010 | Garamszegi | |
| 7,717,942 B2 | 5/2010 | Schumacher | |
| 7,722,617 B2 | 5/2010 | Young | |
| 7,771,430 B2 | 8/2010 | Jones | |
| 7,776,074 B2 | 8/2010 | Bray | |
| 7,799,031 B2 | 9/2010 | Miller | |
| 7,815,664 B2 | 10/2010 | Sherman | |
| 7,824,413 B2 | 11/2010 | Varieur | |
| 7,862,587 B2 | 1/2011 | Jackson | |
| 7,909,835 B2 | 3/2011 | Oribe | |
| 7,922,749 B2 | 4/2011 | Dewey | |
| 7,927,334 B2 | 4/2011 | Miller | |
| 7,927,360 B2 | 4/2011 | Pond | |
| 7,931,654 B2 | 4/2011 | Jones | |
| 7,947,046 B2 | 5/2011 | Justis | |
| 7,985,242 B2 | 7/2011 | Forton | |
| 7,988,694 B2 | 8/2011 | Barrus | |
| 7,988,698 B2 | 8/2011 | Rosenberg | |
| 8,025,682 B2 | 9/2011 | Mahoney | |
| D649,243 S | 11/2011 | Barry | |
| 8,066,739 B2 | 11/2011 | Jackson | |
| 8,096,996 B2 | 1/2012 | Gutierrez | |
| 8,128,629 B2 | 3/2012 | Barry | |
| 8,142,436 B2 | 3/2012 | Kirschman | |
| 8,142,437 B2 | 3/2012 | Mclean | |
| 8,147,524 B2 | 4/2012 | Piza Vallespir | |
| 8,172,847 B2 | 5/2012 | Dziedzic | |
| 8,192,438 B2 | 6/2012 | Garamszegi | |
| 8,197,519 B2 | 6/2012 | Schlaepfer | |
| 8,206,394 B2 | 6/2012 | Stad | |
| 8,211,111 B2 | 7/2012 | Dauster | |
| 8,216,240 B2 | 7/2012 | Dewey | |
| 8,235,997 B2 | 8/2012 | Hoffman | |
| 8,236,032 B2 | 8/2012 | Ramsay | |
| 8,246,623 B2 | 8/2012 | Peultier | |
| 8,292,892 B2 | 10/2012 | Jackson | |
| 8,303,595 B2 | 11/2012 | Jones | |
| 8,308,729 B2 | 11/2012 | Nunley | |
| 8,308,774 B2 | 11/2012 | Hoffman | |
| 8,317,796 B2 | 11/2012 | Stihl | |
| 8,377,065 B2 | 2/2013 | Kuntz | |
| 8,388,659 B1 | 3/2013 | Lab | |
| 8,439,952 B2 | 5/2013 | Geist | |
| 8,449,549 B2 | 5/2013 | Barry | |
| 8,454,664 B2 | 6/2013 | Mclean | |
| 8,460,308 B2 | 6/2013 | Marino | |
| 8,512,343 B2 | 8/2013 | Dziedzic | |
| 8,512,344 B2 | 8/2013 | Hoffman | |
| 8,535,318 B2 | 9/2013 | Peterson | |
| 8,540,718 B2 | 9/2013 | Dauster | |
| 8,545,505 B2 | 10/2013 | Sandstrom | |
| 8,551,141 B2 | 10/2013 | Gephart | |
| 8,556,904 B2 | 10/2013 | Rezach | |
| 8,603,094 B2 | 12/2013 | Walker | |
| 8,608,746 B2 | 12/2013 | Kolb | |
| 8,617,165 B2 | 12/2013 | Harper | |
| 8,663,292 B2 | 3/2014 | Dec | |
| 8,672,944 B2 | 3/2014 | Boachie-Adjei | |
| 8,679,128 B2 | 3/2014 | Seelig | |
| 8,685,029 B2 | 4/2014 | Dziedzic | |
| 8,747,409 B2 | 6/2014 | Ichelmann | |
| 8,764,756 B2 | 7/2014 | Jones | |
| 8,777,953 B1 | 7/2014 | Khalili | |
| 8,790,348 B2 | 7/2014 | Stad | |
| 8,828,006 B2 | 9/2014 | Semler | |
| 8,864,767 B2 | 10/2014 | Blain | |
| 8,888,819 B2 | 11/2014 | Frasier | |
| 8,900,240 B2 * | 12/2014 | White et al. | 606/86 A |
| 8,900,248 B2 | 12/2014 | Biyani | |
| 8,911,442 B2 | 12/2014 | Wing | |
| 8,932,296 B2 | 1/2015 | Neary | |
| 8,956,360 B2 | 2/2015 | Boachie-Adjei | |
| 8,961,523 B2 | 2/2015 | Barrus | |
| 8,979,848 B2 | 3/2015 | Butters | |
| 8,992,536 B2 | 3/2015 | Piza Vallespir | |
| 8,998,958 B2 | 4/2015 | Dauster | |
| 9,005,204 B2 | 4/2015 | Manninen | |
| 9,005,260 B2 | 4/2015 | Dauster | |
| 9,050,139 B2 | 6/2015 | Jackson | |
| 9,066,763 B2 | 6/2015 | Khoo | |
| 2002/0016595 A1 | 2/2002 | Michelson | |
| 2002/0072750 A1 | 6/2002 | Jackson | |
| 2002/0072751 A1 | 6/2002 | Jackson | |
| 2002/0095153 A1 | 7/2002 | Jones | |
| 2002/0133159 A1 | 9/2002 | Jackson | |
| 2003/0023243 A1 | 1/2003 | Biedermann | |
| 2003/0028195 A1 | 2/2003 | Bette | |
| 2003/0032957 A1 | 2/2003 | McKinley | |
| 2003/0187445 A1 | 10/2003 | Keith | |
| 2003/0199872 A1 | 10/2003 | Markworth | |
| 2003/0225408 A1 | 12/2003 | Nichols | |
| 2003/0236529 A1 | 12/2003 | Shluzas | |
| 2004/0039383 A1 | 2/2004 | Jackson | |
| 2004/0049196 A1 | 3/2004 | Jackson | |
| 2004/0147936 A1 | 7/2004 | Rosenberg | |
| 2004/0158247 A1 | 8/2004 | Sitiso | |
| 2004/0162560 A1 | 8/2004 | Raynor | |
| 2004/0167523 A1 | 8/2004 | Jackson | |
| 2004/0167524 A1 | 8/2004 | Jackson | |
| 2004/0167525 A1 | 8/2004 | Jackson | |
| 2004/0167526 A1 | 8/2004 | Jackson | |
| 2004/0254576 A1 | 12/2004 | Dunbar | |
| 2004/0267275 A1 | 12/2004 | Cournoyer | |
| 2005/0010220 A1 | 1/2005 | Casutt | |
| 2005/0038430 A1 | 2/2005 | McKinley | |
| 2005/0059969 A1 | 3/2005 | McKinley | |
| 2005/0119667 A1 | 6/2005 | Leport | |
| 2005/0149048 A1 | 7/2005 | Leport | |
| 2005/0171540 A1 | 8/2005 | Lim | |
| 2005/0182410 A1 | 8/2005 | Jackson | |
| 2005/0187549 A1 | 8/2005 | Jackson | |
| 2005/0192579 A1 | 9/2005 | Jackson | |
| 2005/0192587 A1 | 9/2005 | Lim | |
| 2005/0228392 A1 | 10/2005 | Keyer | |
| 2005/0261687 A1 | 11/2005 | Garamszegi | |
| 2005/0261702 A1 | 11/2005 | Oribe | |
| 2006/0009773 A1 | 1/2006 | Jackson | |
| 2006/0009775 A1 | 1/2006 | Dec | |
| 2006/0025768 A1 | 2/2006 | Iott | |
| 2006/0025769 A1 | 2/2006 | Dick | |

(56) References Cited

U.S. PATENT DOCUMENTS

| | | |
|---|---|---|
| 2006/0025771 A1 | 2/2006 | Jackson |
| 2006/0036254 A1 | 2/2006 | Lim |
| 2006/0036260 A1 | 2/2006 | Runco |
| 2006/0069391 A1 | 3/2006 | Jackson |
| 2006/0079909 A1 | 4/2006 | Runco |
| 2006/0083603 A1 | 4/2006 | Jackson |
| 2006/0089651 A1 | 4/2006 | Trudeau |
| 2006/0095035 A1 | 5/2006 | Jones |
| 2006/0111713 A1 | 5/2006 | Jackson |
| 2006/0111715 A1 | 5/2006 | Jackson |
| 2006/0111730 A1 | 5/2006 | Hay |
| 2006/0149235 A1 | 7/2006 | Jackson |
| 2006/0149238 A1 | 7/2006 | Sherman |
| 2006/0166534 A1 | 7/2006 | Brumfield |
| 2006/0184178 A1 | 8/2006 | Jackson |
| 2006/0247630 A1 | 11/2006 | Iott |
| 2006/0253120 A1 | 11/2006 | Anderson |
| 2006/0264934 A1 | 11/2006 | Fallin |
| 2006/0271050 A1 | 11/2006 | Piza Vallespir |
| 2006/0276789 A1 | 12/2006 | Jackson |
| 2006/0293661 A1 | 12/2006 | Bray |
| 2006/0293690 A1 | 12/2006 | Abdelgany |
| 2006/0293692 A1 | 12/2006 | Whipple |
| 2007/0032162 A1* | 2/2007 | Jackson ................... 446/1 |
| 2007/0043378 A1 | 2/2007 | Kumar |
| 2007/0093817 A1 | 4/2007 | Barrus |
| 2007/0093849 A1 | 4/2007 | Jones |
| 2007/0161998 A1 | 7/2007 | Whipple |
| 2007/0162010 A1 | 7/2007 | Chao |
| 2007/0213714 A1 | 9/2007 | Justis |
| 2007/0213722 A1 | 9/2007 | Jones |
| 2007/0233072 A1 | 10/2007 | Dickinson |
| 2007/0255284 A1 | 11/2007 | Miller |
| 2007/0270868 A1 | 11/2007 | Dewey |
| 2007/0270869 A1 | 11/2007 | Young |
| 2007/0276379 A1 | 11/2007 | Miller |
| 2007/0282337 A1 | 12/2007 | Garamszegi |
| 2007/0288002 A1 | 12/2007 | Carls |
| 2007/0299450 A1 | 12/2007 | Her |
| 2008/0009864 A1 | 1/2008 | Forton |
| 2008/0015601 A1 | 1/2008 | Castro |
| 2008/0039848 A1 | 2/2008 | Jackson |
| 2008/0045950 A1 | 2/2008 | Dewey |
| 2008/0045953 A1 | 2/2008 | Garamszegi |
| 2008/0045955 A1 | 2/2008 | Berrevoets |
| 2008/0045970 A1 | 2/2008 | Saidha |
| 2008/0051781 A1 | 2/2008 | Geist |
| 2008/0051794 A1 | 2/2008 | Dec |
| 2008/0086132 A1 | 4/2008 | Biedermann |
| 2008/0091213 A1 | 4/2008 | Jackson |
| 2008/0119852 A1 | 5/2008 | Dalton |
| 2008/0154277 A1 | 6/2008 | Machalk |
| 2008/0172062 A1 | 7/2008 | Donahue |
| 2008/0177269 A1 | 7/2008 | Seelig |
| 2008/0195155 A1 | 8/2008 | Hoffman |
| 2008/0221583 A1 | 9/2008 | Sharifi-Mehr |
| 2008/0221626 A1 | 9/2008 | Butters |
| 2008/0228233 A1 | 9/2008 | Hoffman |
| 2008/0234678 A1 | 9/2008 | Gutierrez |
| 2008/0234765 A1 | 9/2008 | Frasier |
| 2008/0243190 A1 | 10/2008 | Dziedzic |
| 2008/0300638 A1 | 12/2008 | Beardsley |
| 2008/0319477 A1 | 12/2008 | Justis |
| 2009/0012567 A1 | 1/2009 | Biedermann |
| 2009/0018593 A1 | 1/2009 | Barrus |
| 2009/0030420 A1 | 1/2009 | Runco |
| 2009/0062858 A1 | 3/2009 | Dziedzic |
| 2009/0062859 A1 | 3/2009 | Mahoney |
| 2009/0062860 A1 | 3/2009 | Frasier |
| 2009/0088764 A1 | 4/2009 | Stad |
| 2009/0105712 A1 | 4/2009 | Dauster |
| 2009/0149887 A1 | 6/2009 | Schlaepfer |
| 2009/0157125 A1* | 6/2009 | Hoffman ............ A61B 17/7091 606/86 A |
| 2009/0163956 A1 | 6/2009 | Biedermann |
| 2009/0163962 A1 | 6/2009 | Dauster |
| 2009/0228053 A1 | 9/2009 | Kolb |
| 2009/0228054 A1 | 9/2009 | Hoffman |
| 2009/0228055 A1 | 9/2009 | Jackson |
| 2009/0228056 A1 | 9/2009 | Jackson |
| 2009/0234395 A1 | 9/2009 | Hoffman |
| 2009/0240292 A1 | 9/2009 | Butler |
| 2009/0254125 A1 | 10/2009 | Predick |
| 2009/0281582 A1 | 11/2009 | Villa |
| 2009/0299414 A1 | 12/2009 | Jackson |
| 2009/0306721 A1 | 12/2009 | Kirschman |
| 2010/0024487 A1 | 2/2010 | Khoo |
| 2010/0036432 A1 | 2/2010 | Ely |
| 2010/0036434 A1 | 2/2010 | Ely |
| 2010/0057126 A1 | 3/2010 | Hestad |
| 2010/0063552 A1 | 3/2010 | Chin |
| 2010/0121385 A1 | 5/2010 | Blain |
| 2010/0121386 A1 | 5/2010 | Peultier |
| 2010/0137875 A1 | 6/2010 | Marino |
| 2010/0160921 A1 | 6/2010 | Sun |
| 2010/0179602 A1 | 7/2010 | Dauster |
| 2010/0185248 A1 | 7/2010 | Barry |
| 2010/0198272 A1 | 8/2010 | Keyer |
| 2010/0228302 A1 | 9/2010 | Dauster |
| 2010/0262198 A1 | 10/2010 | Braunschweiler |
| 2010/0292742 A1 | 11/2010 | Stad |
| 2010/0298838 A1 | 11/2010 | Walters |
| 2010/0305625 A1 | 12/2010 | Kuntz |
| 2010/0312279 A1 | 12/2010 | Gephart |
| 2011/0004222 A1 | 1/2011 | Biedermann |
| 2011/0009910 A1 | 1/2011 | Jackson |
| 2011/0015678 A1 | 1/2011 | Jackson |
| 2011/0034962 A1 | 2/2011 | Dunbar |
| 2011/0040328 A1 | 2/2011 | Miller |
| 2011/0040335 A1 | 2/2011 | Stihl |
| 2011/0087298 A1 | 4/2011 | Jones |
| 2011/0093015 A1 | 4/2011 | Ramsay |
| 2011/0118791 A1 | 5/2011 | Nunley |
| 2011/0137358 A1 | 6/2011 | Manninen |
| 2011/0166606 A1 | 7/2011 | Stihl |
| 2011/0166610 A1 | 7/2011 | Altarac |
| 2011/0172714 A1 | 7/2011 | Boachie-Adjei |
| 2011/0184469 A1 | 7/2011 | Ballard |
| 2011/0186787 A1 | 8/2011 | Jiang |
| 2011/0202096 A1* | 8/2011 | White ............ A61B 17/7032 606/86 R |
| 2011/0218583 A1 | 9/2011 | Smith |
| 2011/0257692 A1 | 10/2011 | Sandstrom |
| 2011/0263945 A1 | 10/2011 | Peterson |
| 2011/0282390 A1 | 11/2011 | Hua |
| 2011/0313464 A1 | 12/2011 | Mclean |
| 2011/0313470 A1 | 12/2011 | McLean |
| 2011/0319938 A1 | 12/2011 | Piza Vallespir |
| 2012/0022594 A1 | 1/2012 | Walker |
| 2012/0035668 A1 | 2/2012 | Manninen |
| 2012/0053643 A1 | 3/2012 | Harper |
| 2012/0078308 A1 | 3/2012 | Dziedzic |
| 2012/0083853 A1 | 4/2012 | Boachie-Adjei |
| 2012/0100497 A1 | 4/2012 | Joo |
| 2012/0123431 A1 | 5/2012 | Robinson |
| 2012/0123487 A1 | 5/2012 | Mahar |
| 2012/0143269 A1 | 6/2012 | Ichelmann |
| 2012/0185003 A1 | 7/2012 | Biedermann |
| 2012/0191144 A1 | 7/2012 | Peultier |
| 2012/0197318 A1 | 8/2012 | Barry |
| 2012/0203288 A1 | 8/2012 | Lange |
| 2012/0203291 A1 | 8/2012 | Boulaine |
| 2012/0215266 A1 | 8/2012 | Jones |
| 2012/0271365 A1 | 10/2012 | Daubs |
| 2012/0277808 A1 | 11/2012 | May |
| 2012/0283786 A1 | 11/2012 | Rezach |
| 2012/0303062 A1 | 11/2012 | Amstutz |
| 2013/0018419 A1 | 1/2013 | Rezach |
| 2013/0030445 A1 | 1/2013 | Dauster |
| 2013/0035729 A1 | 2/2013 | Hammer |
| 2013/0046345 A1 | 2/2013 | Jones |
| 2013/0066385 A1 | 3/2013 | Benoist |
| 2013/0066386 A1 | 3/2013 | Biedermann |
| 2013/0079827 A1 | 3/2013 | Neary |

(56) References Cited

U.S. PATENT DOCUMENTS

| | | |
|---|---|---|
| 2013/0085536 A1 | 4/2013 | Biedermann |
| 2013/0090697 A1 | 4/2013 | George |
| 2013/0110124 A1 | 5/2013 | Gleason |
| 2013/0110184 A1 | 5/2013 | Wing |
| 2013/0184763 A1 | 7/2013 | McClintock |
| 2013/0190822 A1 | 7/2013 | Rezach |
| 2013/0245692 A1 | 9/2013 | Hayes |
| 2013/0253598 A1 | 9/2013 | Jackson |
| 2013/0304130 A1 | 11/2013 | Jackson |
| 2013/0345759 A1 | 12/2013 | Meyer |
| 2014/0031872 A1 | 1/2014 | Jackson |
| 2014/0039567 A1 | 2/2014 | Hoefer |
| 2014/0058464 A1 | 2/2014 | Hutchens |
| 2014/0074105 A1 | 3/2014 | Peultier |
| 2014/0074106 A1 | 3/2014 | Shin |
| 2014/0100613 A1 | 4/2014 | Iott |
| 2014/0107708 A1 | 4/2014 | Biedermann |
| 2014/0148865 A1 | 5/2014 | Hennard |
| 2014/0163625 A1 | 6/2014 | Meyer |
| 2014/0214084 A1 | 7/2014 | Jackson |
| 2014/0214097 A1 | 7/2014 | Jackson |
| 2015/0066042 A1 | 3/2015 | Cummins |
| 2015/0066084 A1 | 3/2015 | Petit |
| 2015/0142060 A1 | 5/2015 | Jackson |

FOREIGN PATENT DOCUMENTS

| | | |
|---|---|---|
| CN | 101732086 A | 6/2010 |
| CN | 201684006 U | 12/2010 |
| CN | 202044328 U | 11/2011 |
| CN | 202146354 U | 2/2012 |
| CN | 202342173 U | 7/2012 |
| DE | 4238339 A1 | 5/1994 |
| DE | 202011102890 U1 | 5/2011 |
| DE | 202012102895 U1 | 8/2012 |
| DE | 102011103252 A1 | 11/2012 |
| EP | 1839606 A1 | 10/2007 |
| EP | 1891904 A1 | 2/2008 |
| EP | 2070485 A1 | 6/2009 |
| EP | 2324787 A1 | 5/2011 |
| EP | 2462889 A1 | 6/2012 |
| EP | 2574297 A1 | 4/2013 |
| EP | 2719347 A1 | 4/2014 |
| FR | 2677242 A1 | 12/1992 |
| FR | 2801492 A1 | 6/2001 |
| FR | 2920663 A1 | 3/2009 |
| FR | 2935093 A1 | 2/2010 |
| FR | 2985166 A1 | 7/2013 |
| JP | 0956736 A | 3/1997 |
| JP | 2003265492 A | 9/2003 |
| JP | 2007298123 A | 11/2007 |
| KR | 20080035999 A | 4/2008 |
| KR | 20140035296 A | 3/2014 |
| RU | 2009136963 A | 4/2011 |
| RU | 2010108859 A | 9/2011 |
| WO | WO-9621396 A1 | 7/1996 |
| WO | WO-02094114 A1 | 11/2002 |
| WO | WO-2005055843 A1 | 6/2005 |
| WO | WO-2005058141 A2 | 6/2005 |
| WO | WO-2005063135 A1 | 7/2005 |
| WO | WO-2010024787 A1 | 3/2010 |
| WO | WO-2010054079 A2 | 5/2010 |
| WO | WO-2011133160 A1 | 10/2011 |
| WO | WO-2012127267 A1 | 9/2012 |
| WO | WO-2012127268 A1 | 9/2012 |
| WO | WO-2013019873 A1 | 2/2013 |
| WO | WO-2013059385 A1 | 4/2013 |
| WO | WO-2013112689 A2 | 8/2013 |
| WO | WO-2013150232 A1 | 10/2013 |
| WO | WO-2013187928 A1 | 12/2013 |
| WO | WO-2014013203 A1 | 1/2014 |

* cited by examiner

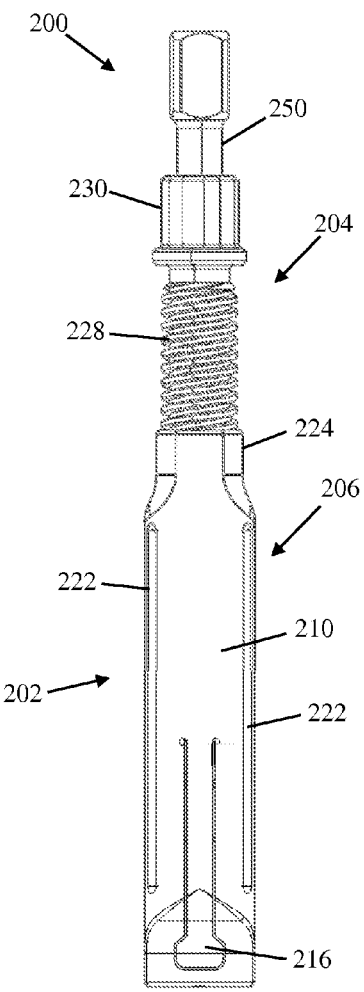
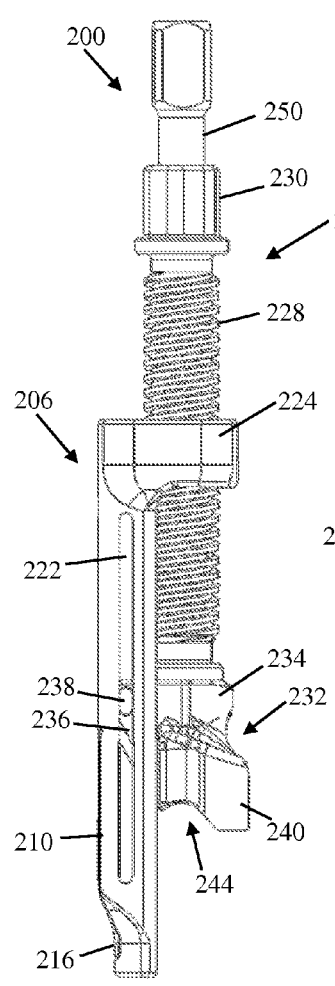
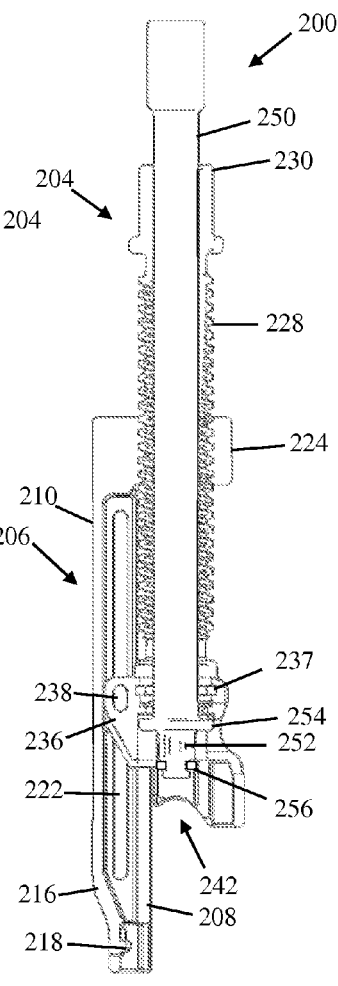
FIG. 15　　FIG. 16　　FIG. 17
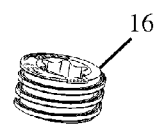
FIG. 18
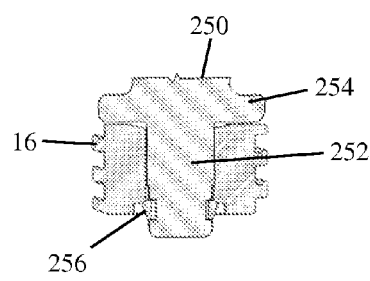
FIG. 19

US 9,486,256 B1

ROD REDUCTION ASSEMBLIES AND RELATED METHODS

CROSS-REFERENCE TO RELATED APPLICATIONS

The present application is a utility patent application that claims priority to U.S. Provisional Application Ser. No. 61/802,046, filed on Mar. 15, 2013, the entire contents of which are hereby expressly incorporated by reference into this disclosure as if set forth fully herein.

FIELD

The present application relates to the field of spinal surgery and spinal fixation devices, including instruments and associated methods for seating or reducing a spinal fixation rod into a fixation anchor during the installation of a spinal fixation construct.

BACKGROUND

Spinal fixation constructs are utilized to provide stability to the spine. Most often the fixation construct is used as an adjunct to fusion surgery during which adjacent vertebrae are prepared to facilitate bone growth between them. Because motion between the vertebrae tends to inhibit bone growth, the fixation constructs are employed to prevent motion so that bone can grow and achieve a solid fusion. When the position of one or more vertebrae must be adjusted to restore a more natural alignment of the spinal column, the fixation construct also serves to maintain the new alignment until fusion is achieved.

Fixation constructs of various forms are known in the art, of which, rod based fixation constructs are one of the most common. Typically in a rod based construct multiple anchors are coupled to a portion (e.g. the posterior elements) of two or more vertebrae and then connected by a fixation rod. The anchors further include a rod housing in which the fixation rod is captured and locked. The rod housing may be fixed or rotatably coupled to the anchor portion and generally includes a pair of upstanding arms separated by a rod channel. When constructing the fixation construct the surgeon must align and seat the rod in the rod channel of each anchor, an undertaking that is generally referred to as "reduction". Reduction can be a challenge, particularly when one or more of the vertebrae to be connected are out of alignment with other vertebrae, and the reduction distance and force requirements can vary greatly from anchor to anchor. Known rod reduction instruments or reducers, can be bulky, time consuming or frustrating to employ, limited in achievable reduction depth, and other issues that can make them less than desirable.

The various reduction instruments described herein are directed towards facilitating simple and efficient rod reduction during installation of a fixation construct.

DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 15 is a back view of the example rod reducer of FIG. 13;

FIG. 16 is a side view of the example rod reducer of FIG. 13;

FIG. 17 is a cross-section view of the example rod reducer of FIG. 13 as viewed in FIG. 16;

FIG. 18 is a perspective view of an example embodiment of a locking cap for use with the reducers of FIGS. 1, 13, and 20;

FIG. 19 is a cross-section view of a the example locking cap of FIG. 18 preloaded onto the reducer of FIG. 13, according to one example embodiment;

DETAILED DESCRIPTION

Figure 1:
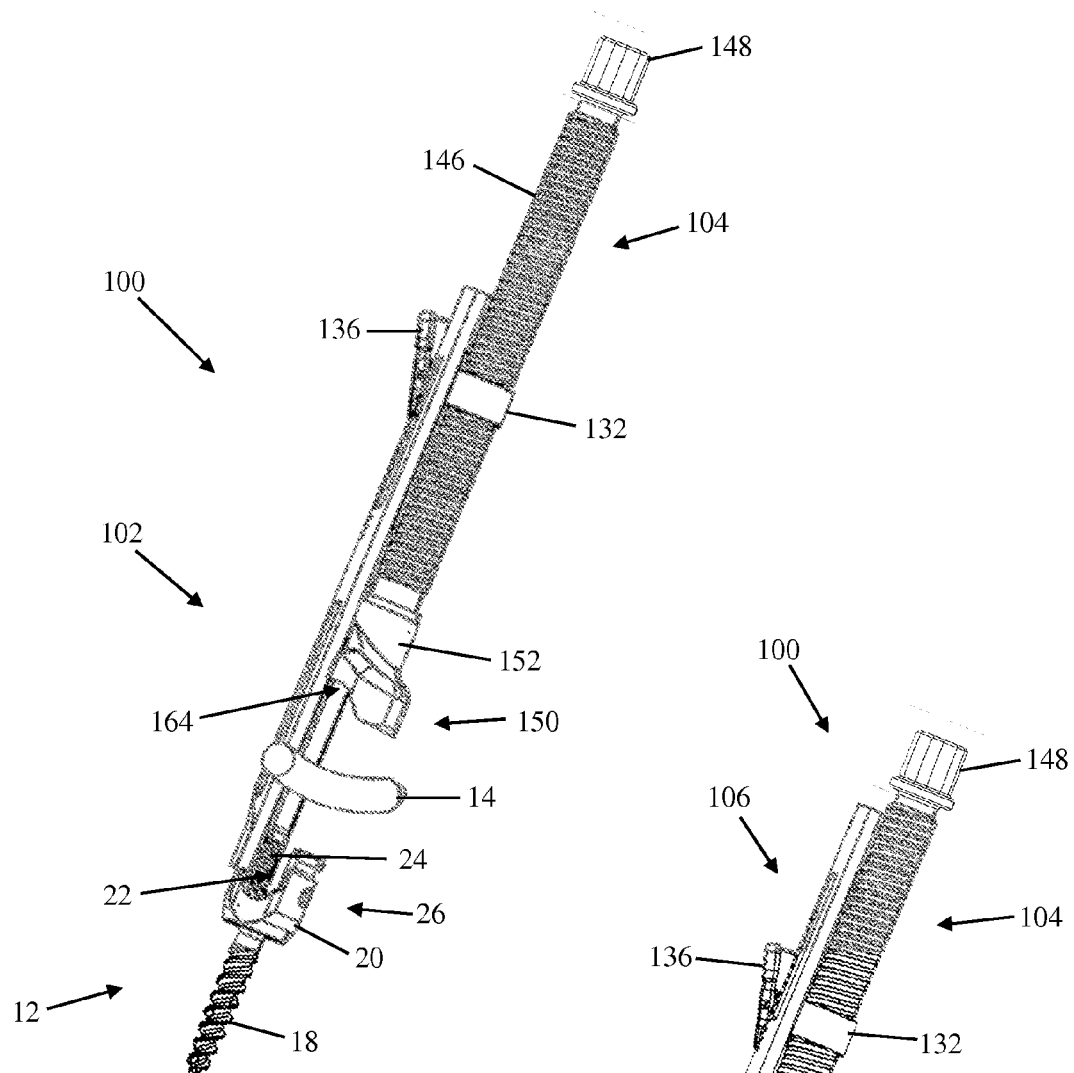
FIG. 1 is a perspective view of a rod reducer for urging a spinal rod to an anchor, according to a first example embodiment.

Various example embodiments of devices and techniques for rod reduction during spinal instrumentation procedures are described herein. In the interest of clarity, not all features of an actual implementation are necessarily described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The rod reduction instruments and related implants, instruments and methods described herein boast a variety of inventive features and components that warrant patent protection, both individually and in combination.

The example reduction assembly, or reducer, embodiments described herein are used during the installation of a fixation construct 10 onto the spine of a patient. The fixation construct 10 includes anchor members 12 connected by a fixation rod 14 locked to each anchor 12. An anchor 12 is implanted in each vertebra to be fixed by the construct 10. For example, two anchors 12 may be used to fix two vertebrae together; three may be used to fix three vertebrae together; four may be used to fix four vertebrae together; and so on. The anchor 12 includes a bone anchor 18 and a housing 20 for capturing and locking a fixation rod 14. The bone anchor 18 may be a bone screw suitable for stable fixation to vertebral bone (e.g. pedicle or vertebral body), as shown. The bone anchor 18 may also include other fixation devices (e.g. hooks, staples, clamps, etc. . . . ). The housing 20 has a base that attaches with the bone anchor and a pair of upstanding arms that together form a rod channel 22. The housing also includes a mechanism 24 to lock the fixation rod 14 in position in the rod channel 22. For example, the mechanism 24 may include a locking cap guide and advancement feature disposed on the interior face of each arm that interacts with a complementary feature on a locking cap 16. The base may be fixed to the anchor 18 or may be coupled such that the housing can rotate in one or more directions (e.g. polyaxial). The housing also includes one or more instrument engagement features 26 for releasably coupling to one or more instruments during implantation. One example of an anchor configured for use with the reducers described herein is shown and described in U.S. patent application Ser. No. 13/456,210, filed Apr. 25, 2012, the entire contents of which are incorporated herein by reference. The reducers described herein can be engaged to one or more of the anchors 12 of the fixation construct 10 to facilitate alignment and advancement of the rod 14 into the rod channel 22 of each anchor.

Figure 2:
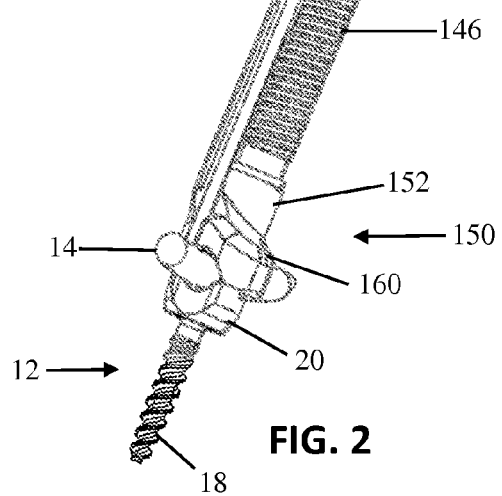
FIG. 2 is a perspective of the example rod reducer of FIG. 1 with the rod in a fully reduced position within the anchor.
Figure 3:
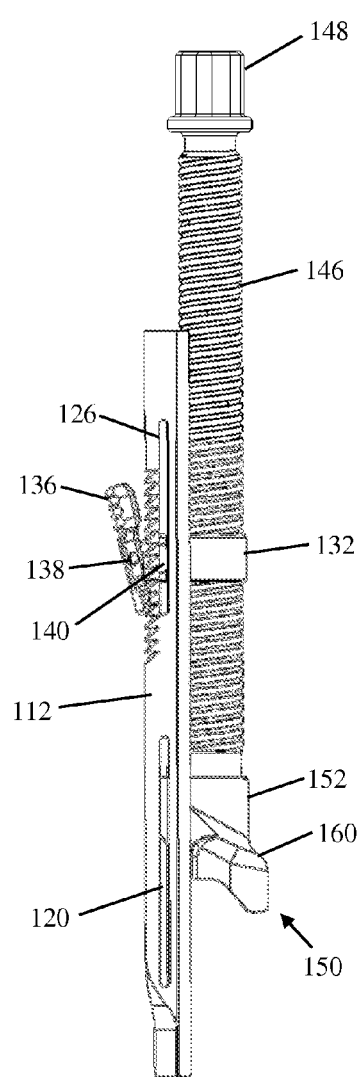
FIG. 3 is a side view of the example rod reducer of FIG. 1.
Figure 4:
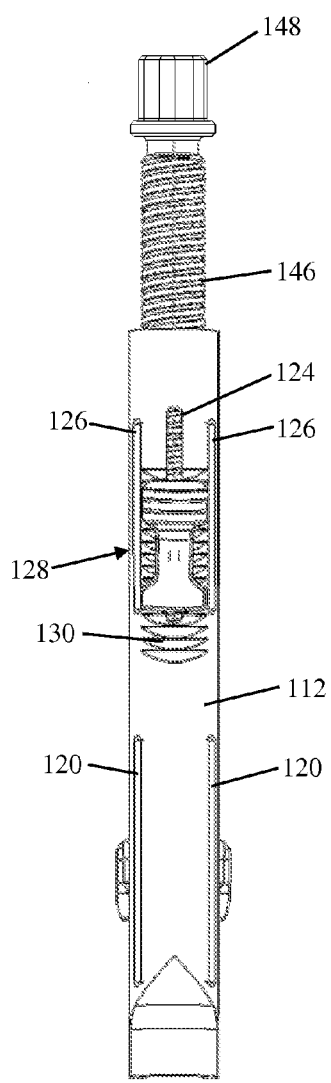
FIG. 4 is a backside view of the example rod reducer of FIG. 1.
Figure 5:
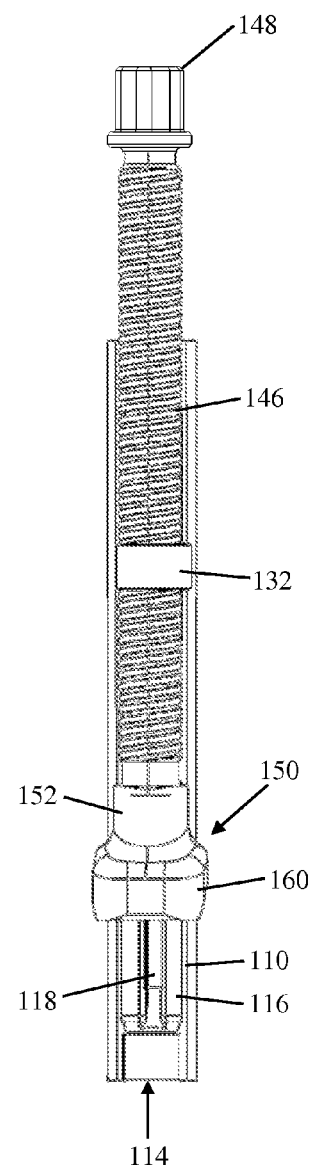
FIG. 5 is a front side view of the example rod reducer of FIG. 1.

With reference to FIGS. 1-12, a reducer 100 according to a first example embodiment is illustrated. As depicted in FIG. 1 the reducer 100 is configured to couple to a single side or arm of anchor 12 (advantageously reducing bulk in the surgical corridor) and impart a downward force on the rod 14. The downward force on the rod acts to draw the rod and anchor housing 20 together until the rod 14 fully seats in the rod channel 22, as shown in FIG. 2. A locking mechanism, such as locking cap 16 (see FIG. 18), may then be at least partially engaged to capture the rod 14 in the housing 20 prior to decoupling the reducer 100 from the anchor 12. The reducer 100 includes a coupling unit 102 unit that connects to the anchor 12 and a translation unit 104 that translates relative to the coupling unit 102 to urge the rod 14 towards the anchor.

Figure 6:
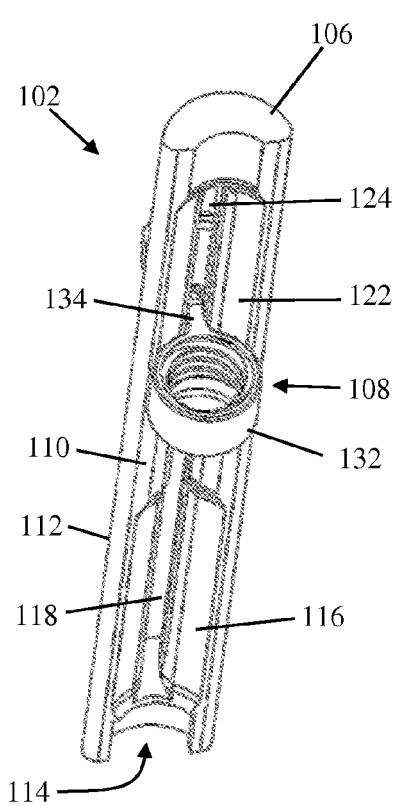
FIG. 6 is a perspective view of a coupling unit of the example rod reducer of FIG. 1.

With reference to FIG. 6, the coupling unit 102 includes a single anchor coupling arm 106 and a translation coupler 108. The anchor coupling arm 106 has a partially cylindrical profile with an inner face 110 and outer face 112. A cavity 114 at the distal end of the coupling arm 106 is dimensioned to snugly receive an arm of the anchor housing 20 therein. Included in the cavity is an engagement feature (not shown) that mates with the instrument engagement features 26 on the anchor to releasably fix the anchor housing 20 to the coupling arm 106. By way of example, the engagement feature may be the same or similar to the engagement feature 216 of reducer 200 described below. Above the cavity 114, the inner face 110 has a lower elongated concave recess 116 with a central slot 118 extending deeper still towards the outer face 112. A lower slot 120 generally coinciding with the length of the recess 116 extends through the coupling arm 106, opening near each edge of the outer face 112 and intersecting the central slot 118. The inner face 110 also includes an upper elongated concave recess 122 with a central slot 124 opening through the outer face. An upper slot 126 generally coinciding with the length of the recess 122 extends through the coupling arm 106, opening near each edge of the outer face 112 and intersecting the central slot 124. The outer face 112 includes a ridge track 128, having a series of downward pointing ridges 130. That is, the ridges 130 have an upper surface that slopes aggressively away and down from the outer face 112. The lower surface of ridges 130 may be perpendicular to the outer face, or preferably, may slope mildly also away and down from the outer face 112.

Figure 9:
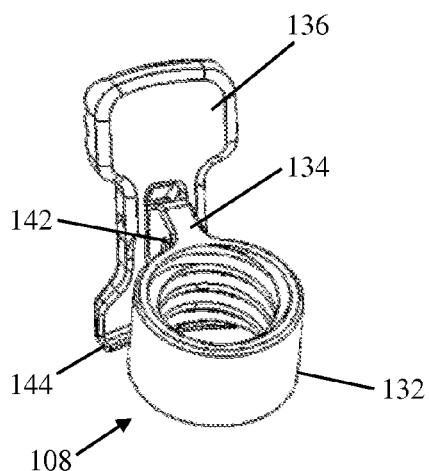
FIG. 9 is a perspective view of a translating coupler of the coupling unit of FIG. 6.

The translation coupler 108, shown in FIG. 9, includes an internally threaded ring 132. A wing 134 extends from the ring 132 through the central slot 124 and is pivotally connected to a switch 136 via pin 138 or other suitable mechanism. A stabilizing bar 140 situated in slot 126 passes through an aperture 142 in the wing 134 to fix the translation coupler 108 to the coupling arm 106 while allowing the translation coupler to translate up and down along the slot 126 and upper recess 122. A pawl 144 at the distal end of the switch 136 engages the ridge track 128 to prevent upward or proximal translation without disengaging the pawl 144. In a preferred example, the switch 136 is spring biased to the engaged pivot position. In this configuration, the application of downward force causes the pawl 144 to slide down the slope of the upper surface of each ridge 130 and automatically return to the engaged position when the pawl 144 passes the lower surface of the ridge 130. Thus, the translation coupler 108 can be advanced distally without manipulating the switch 136 but requires a user to manipulate the switch 136 to disengage the pawl 144 and allow proximal translation.

Figure 7:
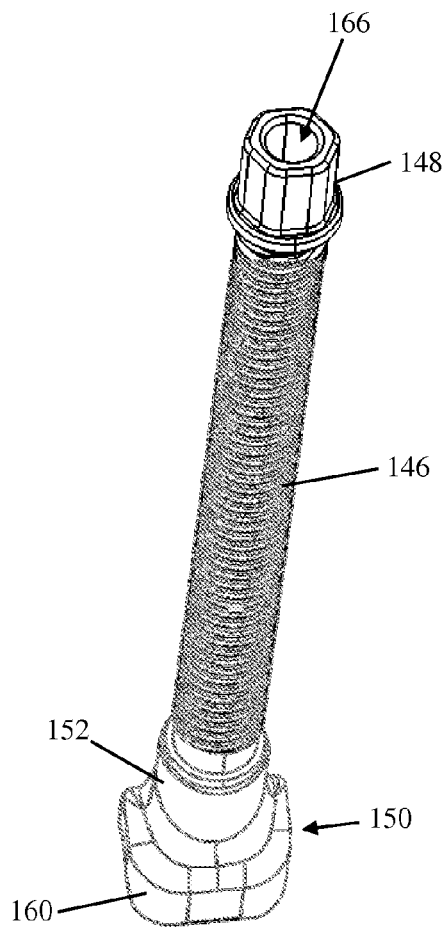
FIG. 7 is a perspective view of a translating unit of the example rod reducer of FIG. 1.
Figure 8:
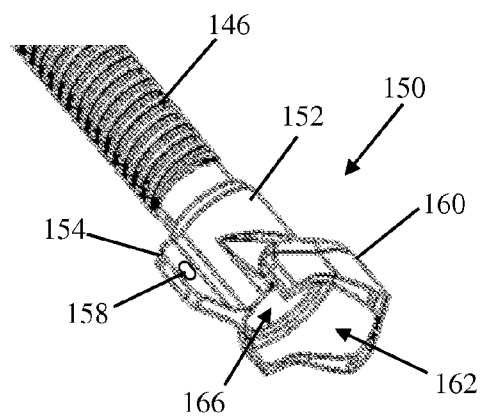
FIG. 8 is another perspective view of the distal end of the translating unit of FIG. 7.

With reference to FIGS. 7-8, the translation unit 104 includes a threaded shaft 146 capped with a drive nut 148 at the proximal end and a foot 150 configured to engage and drive the rod 14 at the distal end. The threaded shaft 146 engages the internal threading of the ring 132 to translate the translation unit 104 relative to the coupling unit 102 upon rotation of the shaft 146. The drive nut 148 can be engaged by a handle (not shown) to facilitate rotation. The foot 150 includes a cylindrical body 152 that complements the lower recess 116 and that is coupled to the shaft 146 in such a way that the foot 150 and shaft 146 are fixed longitudinally but freely rotatable relative to each other. This can be accomplished, for example, with an expansion ring situated in complementary internal and external grooves in the cylindrical body 152 and shaft 146, respectively. Or in one alternative, the distal end of the shaft 146 can include flexible fingers having a ridge that is received in the internal groove of the cylindrical body 152. A wing 154 extends from the cylindrical body and is situated in the central slot 118. A stabilizing bar 156 situated in slot 120 passes through an aperture 158 in the wing 154 to stabilize the foot and eliminate any movement of the foot other than translation up and down along the slot 120 and lower recess 116. A brim 160 extends out and down from the portion of the cylindrical body 152 not in contact with the inner recess 116. An inner cavity 162 enclosed by the brim 160 is configured to receive a portion of the anchor housing 20 therein. The front of brim 160 descends lower than the sides such that a rod recess 164 is formed between the coupling arm 102 and the brim front to help capture and guide the rod into the rod channel 22. Passage 166 extends through the translation unit 104 from the drive nut 148 to the foot 150 to receive locking cap 16 and a driver therethrough to engage the locking cap 16 to the housing 20 prior to removing the reducer 100. The translation unit 104 may further be configured to carry a preloaded locking cap, as illustrated below with respect to reducer 200.

Figure 10A:
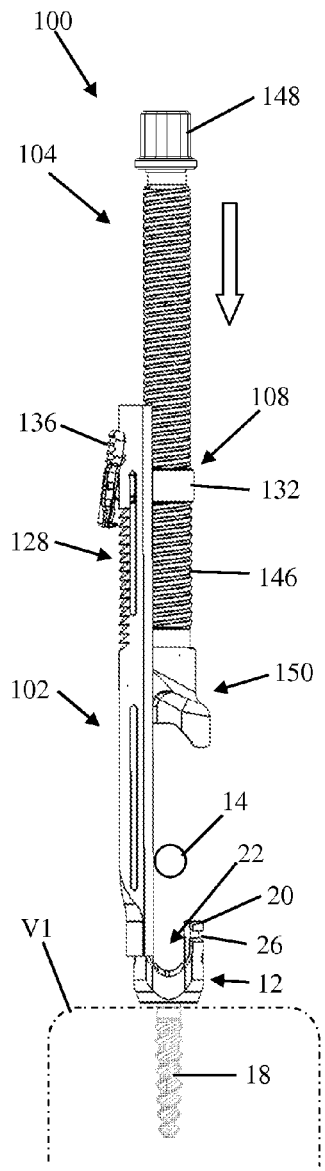
FIGS. 10A-10C are side views of the example reducer of FIG. 1 depicting a sequence for reducing a rod, according to one example embodiment.
Figure 10B:
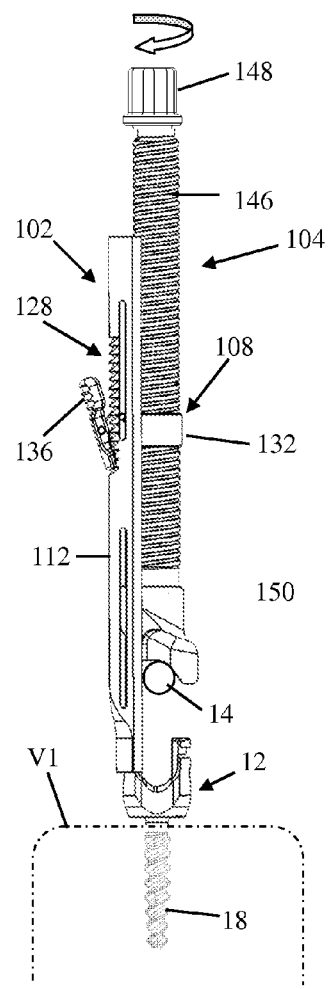
Figure 10C:
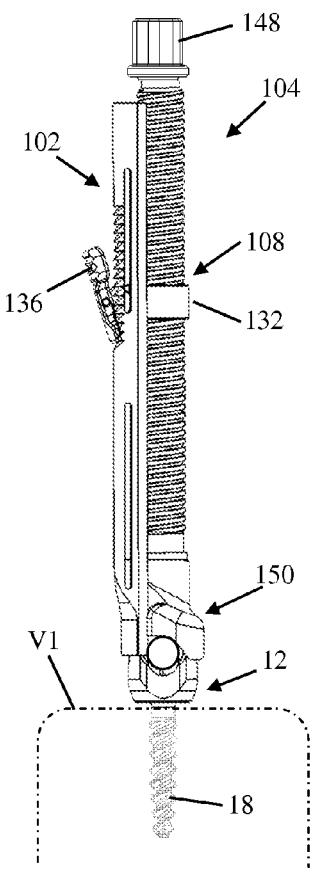
Figures 11, 12:
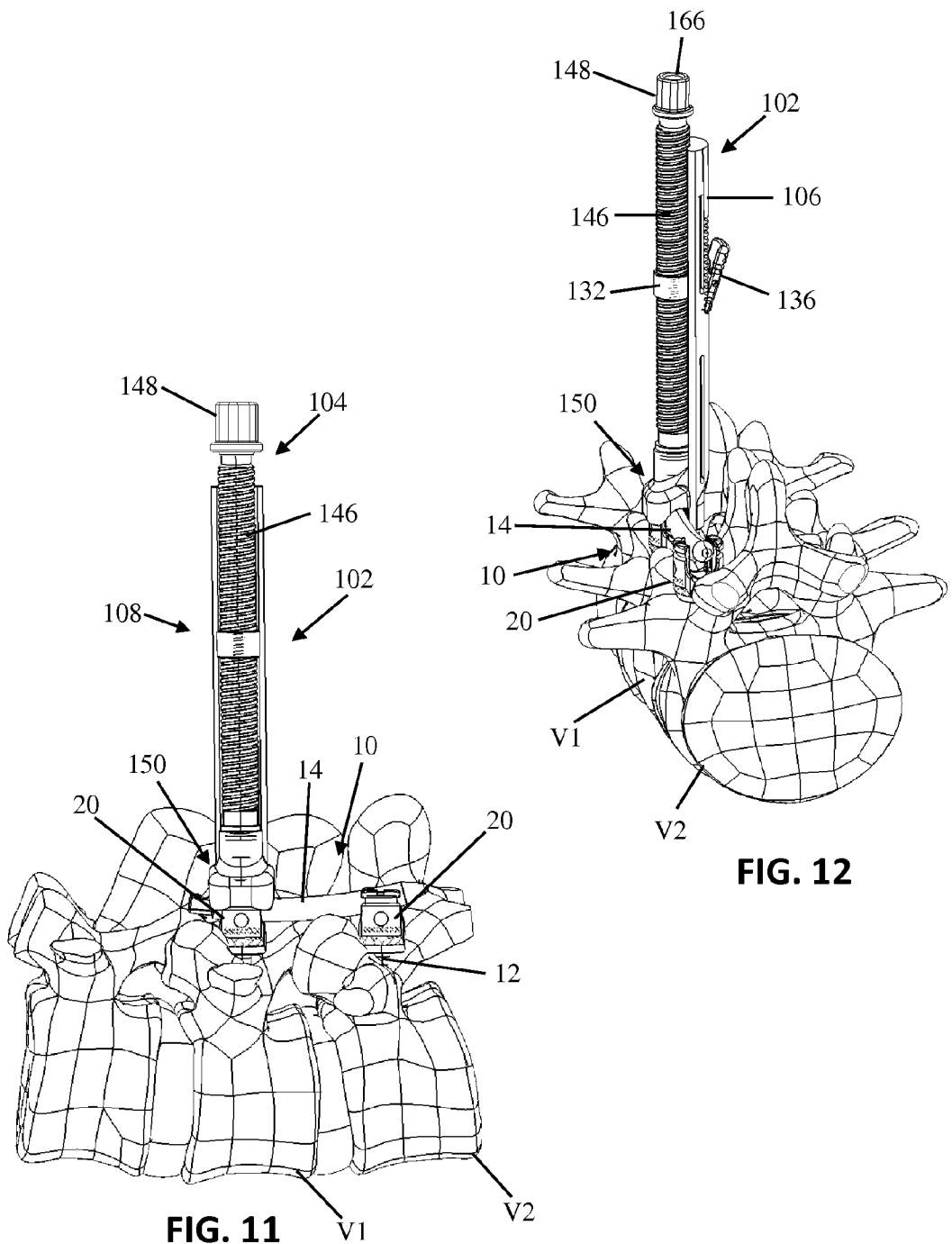
FIGS. 11-12 are lateral and perspective views illustrating the final reduction position shown in 10C in connection with a whole fixation construct fixing two adjacent vertebrae.
Figure 13:
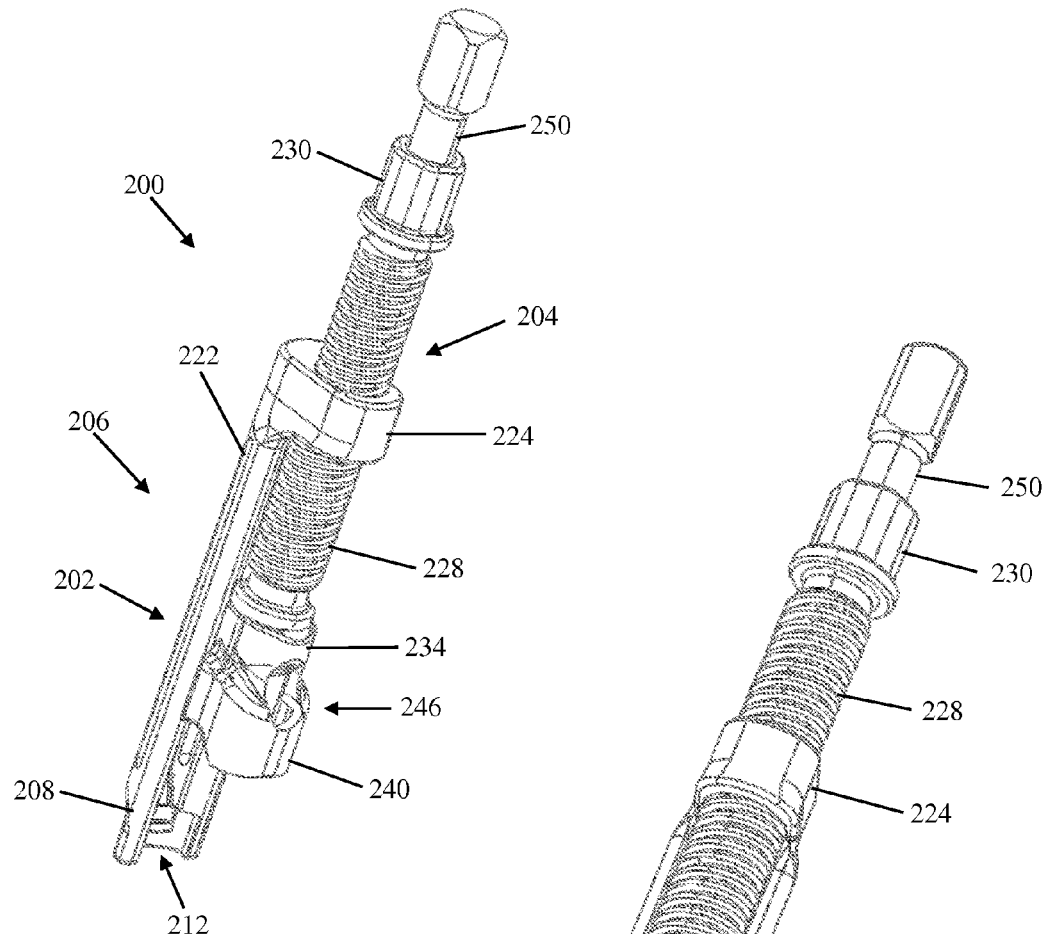
FIG. 13 is a perspective view of a rod reducer according to a second example embodiment.
Figure 14:
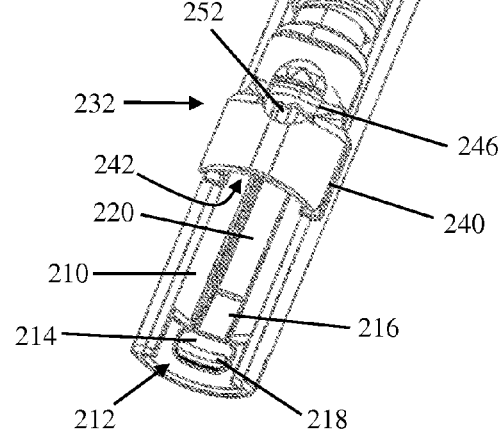
FIG. 14 is a different perspective view of the rod reducer of FIG. 13.

Turning to FIGS. 10A-10C, use of the reducer 100 is illustrated by way of example. Anchors 12 are implanted in each of the vertebra to be fixed, including anchor 12 in vertebra V1 which is the anchor to be reduced in this example, and the rod is inserted to the anchor housings. As seen in FIG. 10A, the rod rests above the housing 20. The distal end of the coupling arm 102 is advanced onto an arm of the anchor housing 20 until the engagement features on the coupling arm 102 engage with the engagement feature 26 of the housing 20. The coupling arm 102 is coupled to the housing with the foot 150 of the translation unit 104 spaced proximal to the housing 20 and the rod 14. The user can then direct force distally onto the translation unit 102 such that the translation coupler 108 translates distally along the coupling arm 102 (translating the translating unit 104 distally along with it). Thus, the translation coupler 108 acts as quick-advance mechanism to advance the translation unit 104 without requiring the added effort and time required to threadingly advance the shaft 146 through the threaded ring 132. As the translation coupler 108 and translation unit 104 are advanced, the pawl 144 engages each ridge 130 on the track 128 in turn to prevent unwanted proximal translation. The translation coupler 108 and translation unit 104 can be advanced this way until the translation unit bottoms out on the slots 124 and/or 126, the foot 150 reaches the rod 14 (FIG. 10B), or beyond that, the force required to further move the rod becomes too great. With the foot 150 in contact with the rod 14, the threaded shaft 146 is rotated to advance the threading through the threaded ring 132 until the rod is fully seated in the anchor housing 20, as shown in FIG. 10C. FIGS. 11 and 12 illustrate this final position shown in 10C with the additional anchor 12 of fixation construct 10 implanted in adjacent vertebra V2. Though shown as a two level construct, additional anchors 12 can be implanted in additional vertebrae to extend the construct 10 over multiple levels. The construct 10 may also be implanted bilaterally with additional anchors 12 and another rod 14 implanted on the contralateral side of the vertebrae V1 and V2. The reducer 100 may be used on any or all of the anchors 12 in the construct. After the rod 14 is fully seated in housing 20 a locking cap 16 can be advanced through the passage 166 and engaged with the locking engagement feature 24 to capture and lock the rod 14 to the anchor 12. The switch 136 can then be manipulated to disengage the pawl 144 from the track 128 retract the translating unit 104 if desired, and the coupling arm 102 is disengaged from the housing 20.

Turning to FIGS. 13-19, a reducer 200 according to a second example embodiment is illustrated. Reducer 200 is similar to reducer 100 and is also configured to couple to a single side or arm of anchor 12. The reducer 200 includes a coupling unit 202 that connects to the anchor 12 and a translation unit 204 that translates relative to the coupling unit 202 to urge the rod 14 towards the anchor. The coupling unit 202 includes a single anchor coupling arm 206. The anchor coupling arm 206 has a partially cylindrical profile with an inner face 208 and an outer face 210. A cavity 212 at the distal end of the coupling arm 206 is dimensioned to snugly receive an arm of the anchor housing 20 therein. An engagement feature 214 includes a flexible finger 216 formed in the coupling arm and having a distal ridge 218 that projects into the cavity 14 to engage the engagement features 26 of the housing 20. The distal surface of the ridge 218 is tapered to automatically deflect the finger 216 outward as the arm of housing 20 is advanced into cavity 212, permitting the ridge 218 to pass the top of the housing until it engages the feature 26. The inner face 208 includes a central slot 220 and a slot 222 that extends through the coupling arm 206 opening near each edge of the outer face 210 and intersecting the central slot 220. A fixed coupling body 224 projects inward from the proximal end of the coupling arm 206 and encloses a threaded passage 226.

The translation unit 204 includes a threaded shaft 228 capped with a drive nut 230 at the proximal end and a foot 232 configured to engage and drive the rod 14 at the distal end. The threaded shaft 228 engages the internal threading of the passage 226. The drive nut 230 can be engaged by a handle (not shown) to facilitate rotation that translates the translation unit 204 relative to the coupling unit 202. The foot 232 includes a generally cylindrical body 234 that complements the inner face 208 and that is coupled to the shaft 228 in such a way that the foot 232 and shaft 228 are fixed translationally but freely rotatable relative to each other. This can be accomplished, for example, with an expansion ring 237 situated in complementary internal and external grooves in the cylindrical body 234 and shaft 228, respectively. Or in one alternative example, the distal end of the shaft 228 can include flexible fingers having a ridge that is received in the internal groove of the cylindrical body 234. A wing 236 extends from the cylindrical body 234 and is situated in the central slot 220. A stabilizing bar 238 situated in slot 222 passes through an aperture in the wing 236 to stabilize the foot and eliminate any movement of the foot other than translation up and down. A brim 240 extends out and down from the portion of the cylindrical body 152 not in contact with the inner face 208. An inner cavity 242 enclosed by the brim 240 is configured to receive a portion of the anchor housing 20 therein. The front of brim 240 descends lower than the sides such that a rod recess 244 is formed between the coupling arm 202 and the brim front to help capture and guide the rod into the rod channel 22. An opening 246 in the front of the foot 232 provides a view into the foot to permit viewing of a preloaded locking cap 16 (not shown).

With reference to FIG. 17, the translation unit 204 further includes a passage 248 extending from the drive nut 230 to the foot 232 in which a drive shaft 250 having a distal drive feature 252 is situated. A rim 254 above the drive feature maintains the drive feature within the foot 232. The drive shaft is permitted to freely translate a limited distance within the passage 248 such that the locking cap may be engaged and fully advanced into the anchor housing 20.

An expansion ring 256 situated in a groove just below the drive feature 252 maintains the locking cap 16 on the drive feature 252 (FIG. 19) until the locking cap 16 is engaged in the housing, after which the drive feature 252 may be removed from the locking cap by pulling up on the drive shaft.

In use the reducer 200 is used similarly to the reducer 100 but without the quick advance translation. Again, anchors 12 are implanted in each of the vertebra to be fixed and the rod is inserted to the anchor housings. The distal end of the coupling arm 202 is advanced onto an arm of the anchor housing 20 until the engagement features 216 on the coupling arm 202 engage with the engagement feature 26 of the housing 20. The coupling arm 202 is coupled to the housing with the foot 232 of the translation unit 204 spaced proximal to the housing 20 and the rod 14. A handle may be coupled to the drive nut 230 and the threaded shaft 228 rotated to advance the threading through the threaded passage 226 translating the foot 232 distally until the rod 14 is fully seated in the anchor housing 20. Again, though shown as a two level construct, additional anchors can be implanted to extend the construct 10 over multiple levels and/or bi-laterally. After the rod 14 is fully seated in housing 20, the drive shaft 250 can be pressed downward and rotated to engage the locking cap 16 with the locking engagement feature 24 to capture and lock the rod 14 to the anchor 12.

Figures 20, 21:
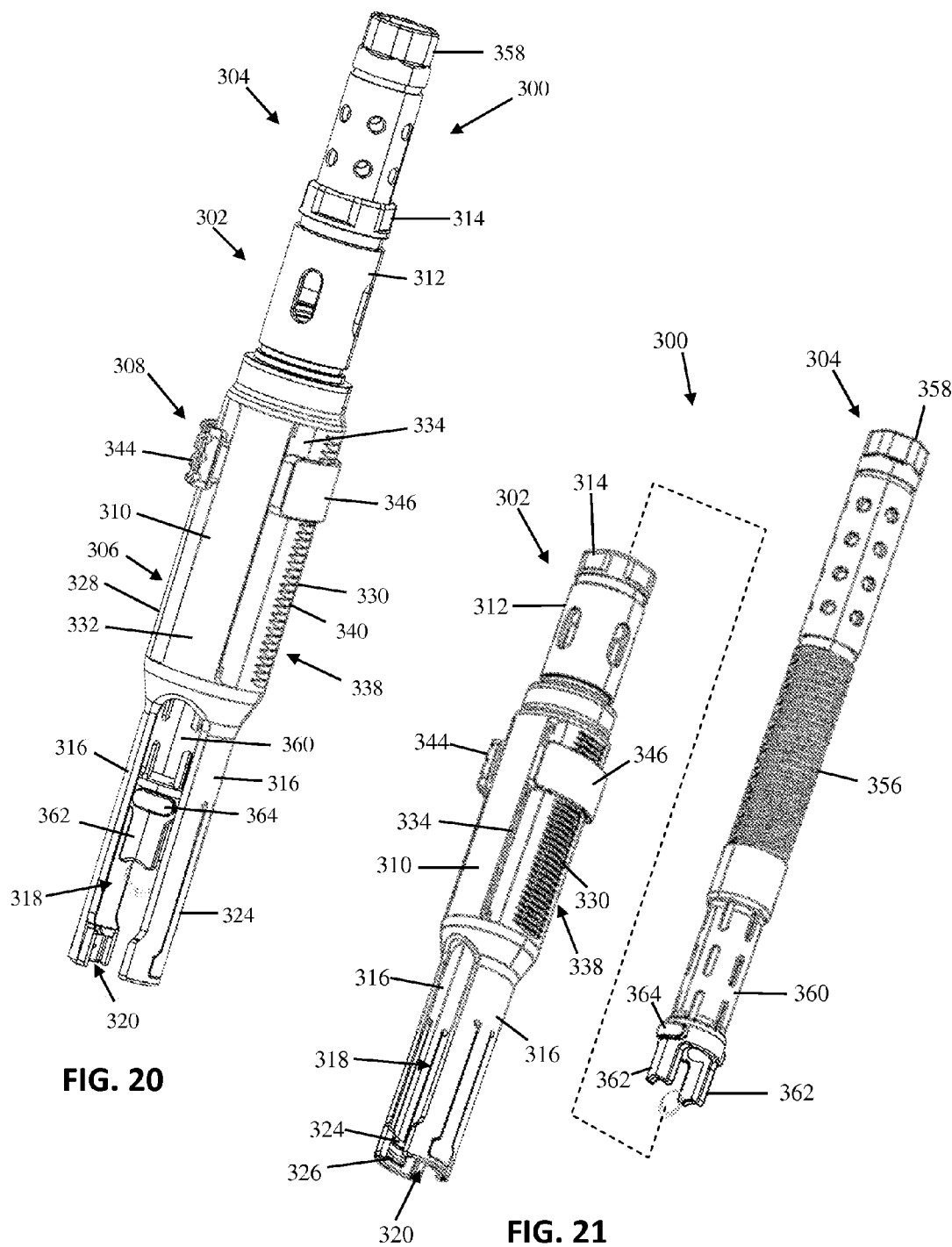
FIG. 20 is a perspective view of a rod reducer according to a third example embodiment.
FIG. 21 is an exploded view illustrating a the coupling unit and translation unit of the example reducer of FIG. 20.
Figure 22:
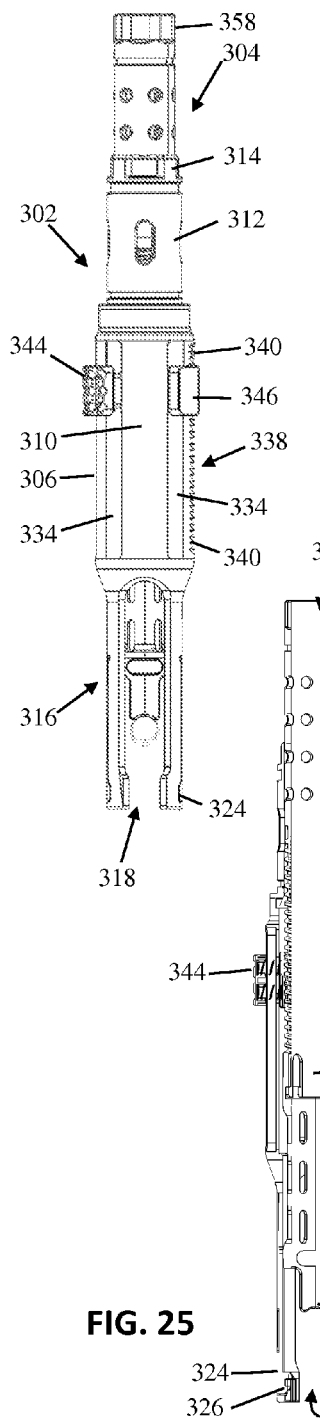
FIG. 22 is a side view of the example rod reducer of FIG. 20.
Figure 23:
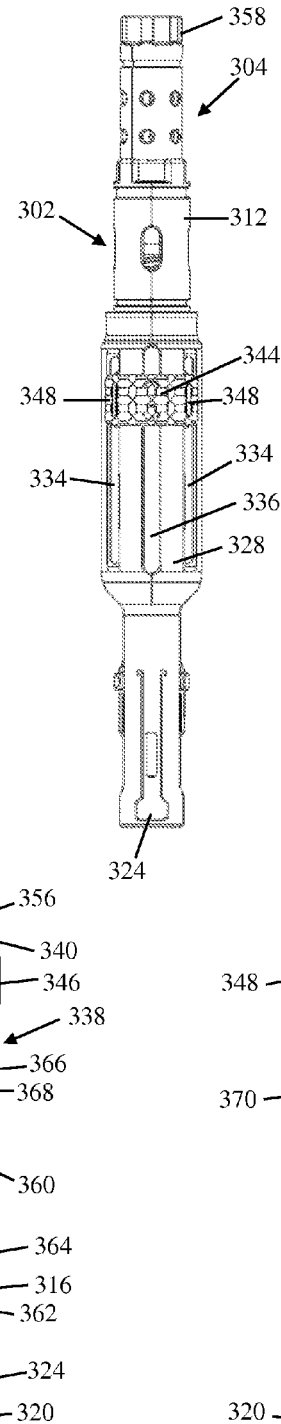
FIG. 23 is a front side view of the example rod reducer of FIG. 20.
Figure 24:
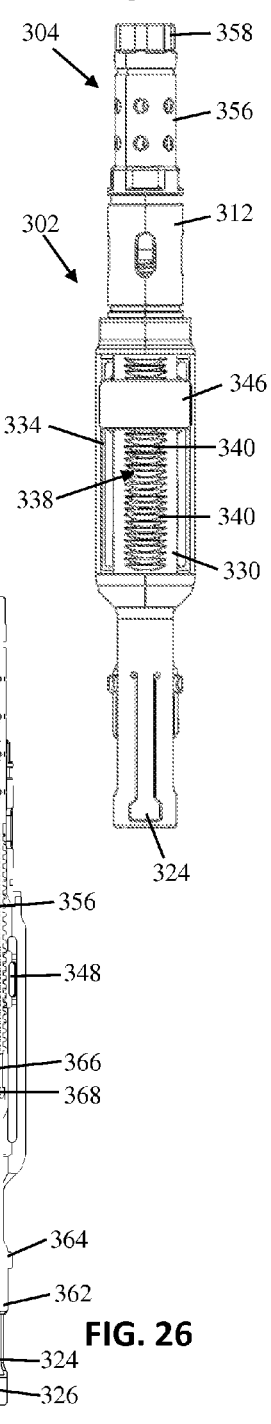
FIG. 24 is a backside view of the example rod reducer of FIG. 20.
Figure 25:
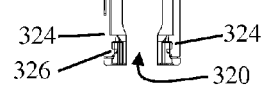
FIG. 25 is a cross-section view of the example rod reducer of FIG. 20 viewed in FIG. 22.
Figure 26:
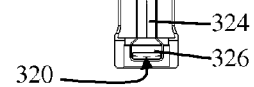
FIG. 26 is a cross-section view of the example rod reducer of FIG. 20 as viewed in FIG. 24.
Figure 27:
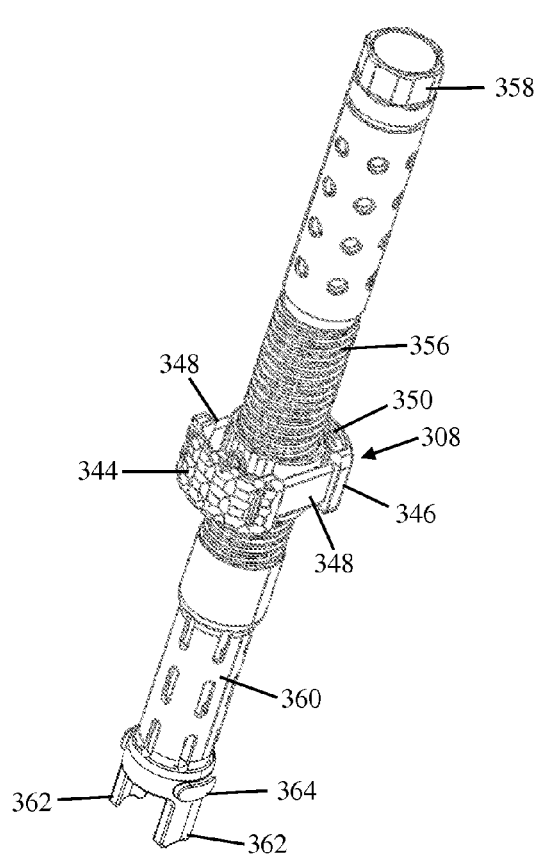
FIG. 27 is a perspective view of a translating unit and translating coupler of the example rod reducer of FIG. 20.

With reference to FIGS. 20-30, a reducer 300 according to a third example embodiment is illustrated. The reducer 300 is configured to couple to an implanted anchor housing 20 and impart a downward force on the rod 14. The downward force on the rod acts to draw the rod and housing 20 together until the rod 14 fully seats in the rod channel 22. A locking mechanism, such as locking cap 16, may then be at least partially engaged to capture the rod 14 in the housing 20 prior to decoupling the reducer 100 from the anchor 12. As illustrated in FIGS. 20-21, the reducer 300 includes a coupling unit 302 unit that connects to the anchor 12 and a translation unit 304 that translates relative to the coupling unit 302 to urge the rod 14 towards the anchor. With reference to FIG. 20, the coupling unit 302 includes an outer sleeve 306 and a translation coupler 308. The outer sleeve 306 has a generally centralized and cylindrical body 310. A connector mast 312 extends proximally from the body 310 and a pair of anchor coupling arms 316 extend distally from the body. The connector mast 312 is capped by a head 314 that is configured to engage with additional instruments if desired. By way of example, the head is configured to mimic the proximal end of the minimally invasive guides described in U.S. patent application Ser. No. 13/456,210 such that any instruments that engage or couple with the guides may also engage or couple with the reducer 300 (for example, vertebral body derotation assemblies, counter torques, etc. ... ). The anchor coupling arms 316 are separated by a channel 318 that aligns with the anchor rod channel 22 when the reducer 300 is coupled to the anchor 12. To couple to the anchor 12, a cavity 320 at the distal end of the coupling arms 316 is dimensioned to snugly receive the arms of the anchor housing 20 therein. An engagement feature 322 is included on each coupling arm. By way of example, the engagement feature 322 includes a flexible finger 324 formed in the coupling arm and having a distal ridge 326 that projects into the cavity 320 to engage the engagement features 26 of the housing 20. The distal surface of the ridges 326 are tapered to automatically deflect the finger 324 outward as the arms of housing 20 are advanced into cavity 320, permitting the ridges 326 to pass the tops of the housing arms until they engages the anchor features 26. This way, the reducer 300 can be positioned over the rod and quickly snapped onto and secured to the anchor with the simple application of downward pressure. To later disengage the reducer 300 from the housing 20 an instrument may be advanced into the channel and manipulated to apply outward pressure to each of the fingers 324.

The body 310 is split into four quadrants including a front wall 328, a back wall 330, and two sidewalls 332. Four elongated side slots 334 separate each wall from the next. An elongated front slot 336 also runs through the middle of the front wall 328. The back wall 330 includes a ridge track 338, having a series of downward pointing ridges 340. That is, the ridges 340 have an upper surface that slopes aggressively away and down from the back wall 330. The lower surface of ridges 340 may be perpendicular to the outer face, or preferably, may slope mildly also away and down from the back wall 330.

Figure 29:
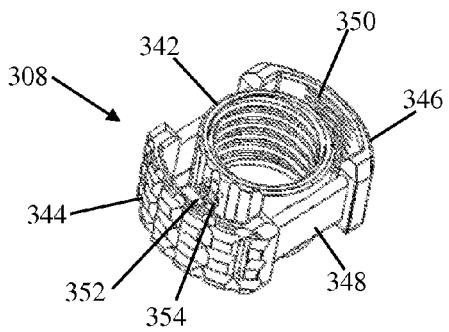
FIG. 29 is a perspective view of the translating coupler of FIG. 27.

The translation coupler 308, shown in FIG. 29, includes an internally threaded ring 342 surrounded by a front plate 344 and a back plate 346. Bars 348 couple the front plate 344 and back plate 346 together and engage cutouts in the outer surface of threaded ring 342 to longitudinally and rotationally fix the ring 342 in position relative to the front and back plates. The bars 348 can slide along the ring 342 cutouts such that the front plate 344 can be moved towards the ring 342 causing the back plate 344 to move farther away from the ring 342, and vice versa. The bars 348 couple the front and back plates through the side slots 334 such that the translation coupler 308 is coupled to body 310 and can translate up and down along the body 310 with the front plate 344 moving along the front wall 328 and the back plate 346 moving along the back wall 330. The inner surface of the back plate 346 includes a row of ridges 350 that are complementary to the ridges 340 of ridge track 338 and thus, inhibit upward or proximal translation of the translation coupler 308 when the ridges 350 and 340 are engaged. The inner surface of the front plate 344 includes a pair of cylindrical spring housings 352 situated centrally one on top of the other. The cylindrical spring housings 352 are dimensioned to pass through the front slot 336. The springs 354 fitted in the housings 352 engage the threaded ring 342 to bias the front plate 344 away from the front wall 328 and the back plate 346 into contact with the back wall 330 and hence the ridge track 338. In this configuration, the application of downward force causes ridges 350 to slide down the sloped upper surfaces of each ridge 340 and automatically return to the engaged position when the ridge 350 passes the lower surface of the ridge 340. Thus, the translation coupler 308 can be advanced distally by the application of downward force, but requires a user to manipulate front plate 344 to disengage the back plate 346 from the back wall 330 and allow proximal translation. Other configurations for lockingly engaging the back plate 346 to the back wall are also contemplated. For example only, instead of the ridge track 338, the side slots 334 adjacent the back wall can have circular cutouts along the slot length. A pair of cylindrical bars can be used on each side to connect the front and back plates instead of the single flat bar 348, the cylindrical bars passing through cylindrical cutouts in the threaded ring 342, and connecting to the back plate 346 via enlarged cylindrical discs that are dimensioned to slide laterally into the circular cutouts but cannot pass from one cutout to the next along the slot 334.

Figure 28:
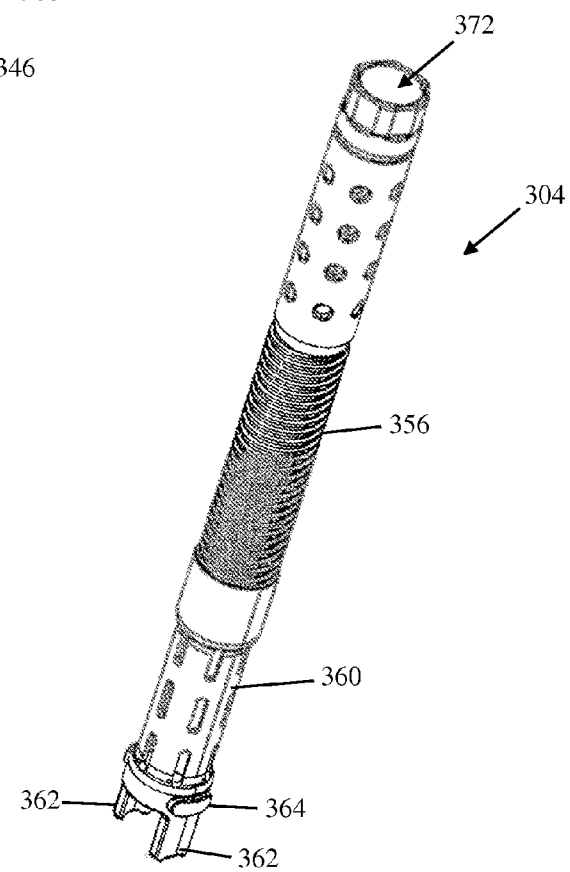
FIG. 28 is a perspective view of the translating unit of FIG. 27.

With reference to FIG. 28, the translation unit 304 includes a shaft 356 capped with a drive nut 358 at the proximal end and a pusher member 360 ending in a pair of reduction arms 362 at the distal end. The reduction arms 362 are situated between the coupling arms 316 and align with the channel 318 on each side. The distal ends of reduction arms 362 are preferably concave in shape to contour to the rod. Protrusions 364 just above each reduction arm 360 on the pusher member 360 slide along the channel 318 between the coupling arms 316 to prevent rotation of the pusher member 360. Along the shaft 356 between the drive nut 358 and pusher member 360 is a threaded region with threading complementary to the threaded ring 342 to translate the translation unit 304 relative to the coupling unit 302 upon rotation of the shaft 356. The drive nut 148 can be engaged by a handle (not shown) to facilitate rotation. The pusher member 360 is coupled to the threaded shaft 356 in such a way that the pusher member and shaft are fixed longitudinally but freely rotatable relative to each other. To accomplish this, by way of example, the distal end of the threaded portion includes flexible fingers 366 each having a ridge 370 that is received in an internal groove 368 of the pusher member 360. A passage 372 extends through the translation unit 104 from the drive nut 148 to reduction arms 360 to receive locking cap 16 and a driver therethrough to engage the locking cap 16 to the housing 20 prior to removing the reducer 300. Alternatively, the translation unit 304 may further be configured to carry a preloaded locking cap, for example, as described and illustrated with respect to reducer 200.

Figures 30A, 30B, 30C:
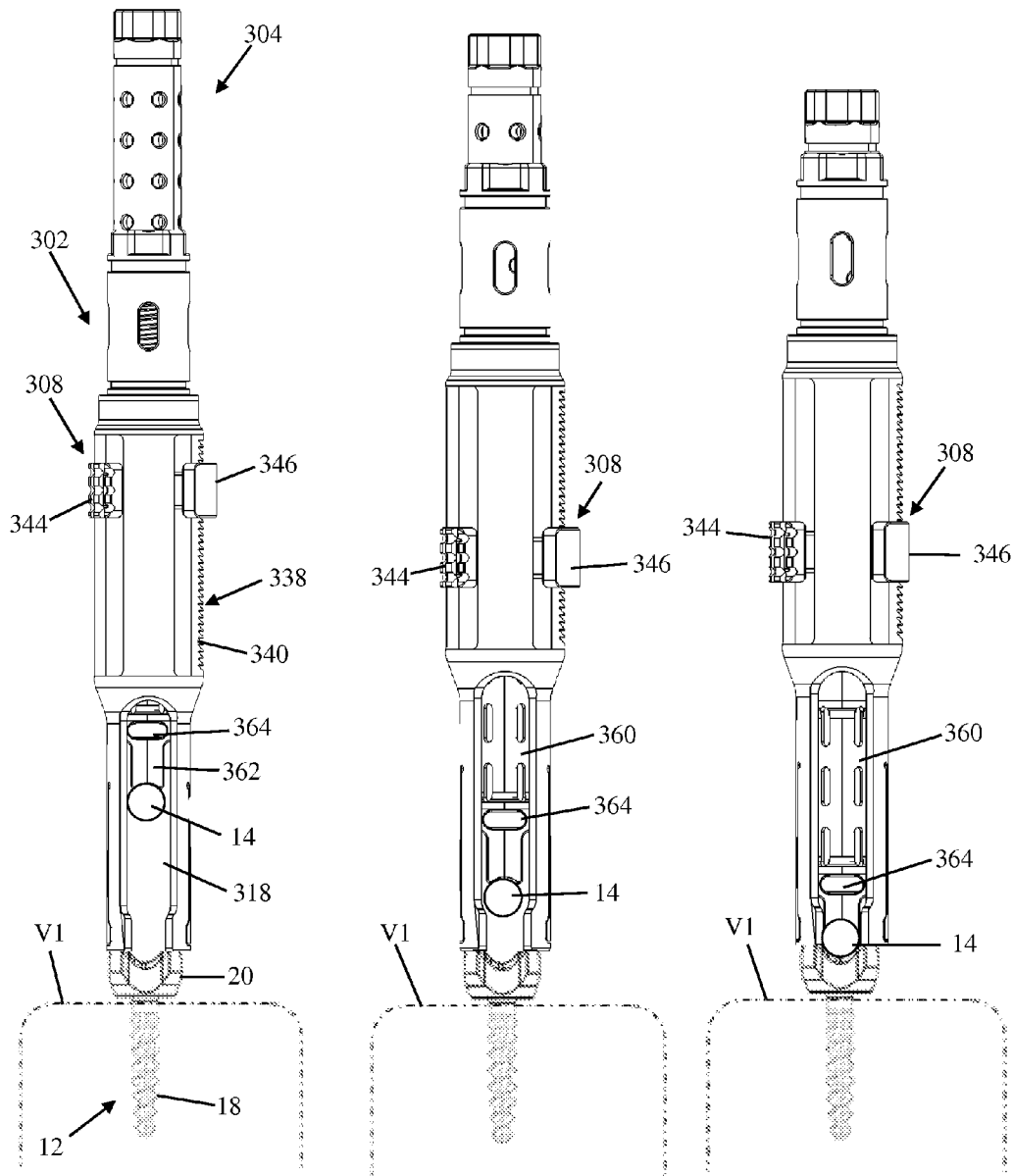
FIGS. 30A-30C are side views of the example reducer of FIG. 20 depicting a sequence for reducing a rod, according to one example embodiment.

Turning to FIGS. 30A-30C, use of the reducer 300 is illustrated by way of example. Anchors 12 are implanted in each of the vertebra to be fixed, including anchor 12 in vertebraV1 which is the anchor to be reduced in this example, and the rod is inserted to the anchor housings. As seen in FIG. 30A, the distal ends of the coupling arms 316 are advanced over the rod such that the rod 14 is captured in the channel 318 and onto the anchor housing 20 until the engagement features 324 engage the features 26 on the housing. The user can then direct force distally onto the translation unit 304 such that the translation coupler 308 translates distally along the body 310 (translating the translating unit 304 distally along with it). Thus, the translation coupler 308 acts as quick-advance mechanism to advance the translation unit 304 without requiring the added effort and time required to threadingly advance the shaft 356 through the threaded ring 342. As the translation coupler 308 and translation unit 304 are advanced, the back plate ridges 350 engage each ridge 340 on the track 338 in turn to prevent unwanted proximal translation. The translation coupler 308 and translation unit 304 can be advanced this way until the translation unit bottoms out on the slots 334, the reduction arms 360 reach the rod 14 (FIG. 30B), or beyond that, the force required to further move the rod becomes too great or a more controlled and precise reduction is desired. With the reduction arms 360 in contact with the rod 14, the threaded shaft 356 is rotated to advance the threading through the threaded ring 342 until the rod is fully seated in the anchor housing 20, as shown in FIG. 30C. Though shown as a two level construct, additional anchors 12 can be implanted in additional vertebrae to extend the construct 10 over multiple levels and/or bilaterally with additional anchors 12 and another rod 14 implanted on the contralateral side of the vertebrae. The reducer 300 may be used on any or all of the anchors 12 in the construct. After the rod 14 is fully seated in housing 20 a locking cap 16 can be engaged with the locking engagement feature 24 to capture and lock the rod 14 to the anchor 12. The front plate 344 can then be depressed to disengage the back plate from the track 338 to retract the translating unit 104 if desired, and the reducer 300 disengaged from the housing 20.

While specific embodiments have been shown by way of example in the drawings and described herein in detail, it will be appreciated that the invention is susceptible to various modifications and alternative forms (beyond combining features disclosed herein). The description herein of specific embodiments is not intended to limit the invention to the particular forms disclosed, but on the contrary, the invention is to cover all modifications, equivalents, and alternatives falling within the spirit and scope of the invention.

What is claimed is:

1. A rod reducer for the reduction of spinal rods into a rod-receiving portion of a fixation anchor, comprising:
    an outer sleeve including a cylindrical housing and a pair of anchor coupling arms extending distally from the cylindrical housing, the anchor coupling arms each including an engagement feature configured to releasably couple an arm of a fixation anchor, the coupling arms being spaced apart to define a rod channel therebetween;
    an inner shaft including a distal rod engagement feature that advances distally relative to the coupling arms, the inner shaft being coupled to the outer sleeve via a coupler that drives distal advancement of the distal rod engagement feature via a first threaded advancement mechanism and a second non-threaded advancement mechanism, the coupler including an internally threaded ring and a latch plate locking feature having a front plate and a rear plate connected to each other by first and second side connectors that couple the latch plate to the ring, when engaged the latch plate inhibits proximal advancement of the distal rod engagement feature via the second non-threaded advancement mechanism but does not inhibit distal advancement of the distal rod engagement feature via the second non-threaded advancement mechanism, the first and second side connectors being coupled to the ring such that the latch plate is fixed both rotationally and longitudinally relative to the ring but slides relative to the ring to engage and disengage the latch plate locking feature.

2. The rod reducer of claim 1, wherein the cylindrical housing houses the ring and includes a front wall, back wall, first sidewall and second sidewall, the front wall being separated from the first sidewall by a first side slot and separated from the second sidewall by a second side slot, the back wall being separated from the first sidewall by a third side slot and separated from the second sidewall by a fourth side slot.

3. The rod reducer of claim 2, wherein the front plate is situated adjacent the front wall and the back plate is situated adjacent the back wall, the first side connector extending through the first and third side slots and the second connector extending through the second and fourth side slots.

4. The rod reducer of claim 3, wherein the back wall includes a ridge track and an interior surface of the back plate includes ridges complementary to the ridge track.

5. The rod reducer of claim 4, wherein the latch plate is spring biased to a position relative to the ring in which the back plate ridges engage the ridge track.

6. The rod reducer of claim 3, wherein the third and fourth side slots include a series of circular cutouts and an interior surface of the back wall includes cylindrical discs that are dimensioned to slide laterally in and out of the circular cutouts but cannot pass longitudinally from one circular cutout along the slot to the next.

7. The rod reducer of claim 1, wherein the inner shaft extends through the ring and includes a threaded region threadedly mated with the ring internal threading.

8. The rod reducer of claim 7, wherein the distal rod engagement feature is rotationally free and translationally fixed to the threaded region.

9. The rod reducer of claim 8, wherein the distal rod engagement feature includes a pair of reduction arms situated in the rod channel between the outer sleeve coupling arms.

10. The rod reducer of claim 9, including a longitudinal passage extending through the inner shaft to receive a locking cap and driver therethrough.

11. The rod reducer of claim 1, wherein the engagement feature on each coupling arm of the outer sleeve includes a flexible finger with a distal interior projection.

12. The rod reducer of claim 11, wherein the distal interior projection is a ridge having a tapered distal surface such that the flexible finger automatically deflects outward to permit passage of a fixation anchor arm.

13. The rod reducer of claim 11, wherein the flexible finger is formed within the boundaries of coupling arm.

* * * * *